(12) United States Patent
Brown

(10) Patent No.: US 8,968,759 B2
(45) Date of Patent: Mar. 3, 2015

(54) METHOD OF ADMINISTERING AN INJECTABLE ANTIBIOTIC TO AN ANIMAL

(75) Inventor: Scott A. Brown, Galesburg, MI (US)

(73) Assignee: Zoetis P&U LLC, Florham Park, NJ (US)

( * ) Notice: Subject to any disclaimer, the term of this patent is extended or adjusted under 35 U.S.C. 154(b) by 0 days.

(21) Appl. No.: 12/912,942

(22) Filed: Oct. 27, 2010

(65) Prior Publication Data
US 2011/0098266 A1    Apr. 28, 2011

Related U.S. Application Data

(63) Continuation of application No. 10/391,676, filed on Mar. 19, 2003, now abandoned.

(60) Provisional application No. 60/366,212, filed on Mar. 21, 2002.

(51) Int. Cl.
| | | |
|---|---|---|
| *A61K 31/546* | (2006.01) | |
| *A61K 31/00* | (2006.01) | |
| *A61K 31/496* | (2006.01) | |
| *A61D 7/00* | (2006.01) | |
| *A61K 31/65* | (2006.01) | |
| *A61K 31/7048* | (2006.01) | |

(52) U.S. Cl.
CPC ........... *A61K 31/496* (2013.01); *A61D 7/00* (2013.01); *A61K 31/65* (2013.01); *A61K 31/7048* (2013.01)
USPC ........................................ 424/422; 514/206

(58) Field of Classification Search
None
See application file for complete search history.

(56) References Cited

U.S. PATENT DOCUMENTS

| | | | |
|---|---|---|---|
| 2,883,984 A | 9/1957 | Candido, Jr. et al. | |
| 2,999,020 A | 9/1961 | Williams | |
| 4,902,683 A | 2/1990 | Amin et al. | |
| 5,079,007 A | 1/1992 | Putnam | |
| 5,563,155 A | 10/1996 | Domagala et al. | |
| 6,074,657 A * | 6/2000 | Brown ......................... | 424/423 |

FOREIGN PATENT DOCUMENTS

| | | |
|---|---|---|
| WO | 94/20505 | 9/1994 |
| WO | 98/41207 | 9/1998 |

OTHER PUBLICATIONS

Forg et al. "Superiority of the Ear Pinna over Muscle Tissue as site for DNA Vaccination". Gene Therapy 5; 799-797 1998.*
PCT International Search Report, PCT/US03/08571, mailed Aug. 6, 2003.
Christoffe, "Implants contg. antimicrobial agent—for slow release in animals", Database WPI, Section Ch, Week 199002, Derwent Publications Ltd., London, GB; AN 1990-015187, Oct. 25, 1989.
Foerg et al., "Superiority of the ear pinna over muscle tissue as site for DNA vaccination", Gene Therapy, 5 (6):789-797, 1998.
"1 entry found for bulldogging." Dictionary.com. Online. Internet. Accessed Mar. 8, 2005 (cited in U.S. Appl. No. 10/391,676).
"Pinna." Stedman's Medical Dictionary 27th Edition. Online. Internet. Accessed Mar. 8, 2005 (cited in U.S. Appl. No. 10/391,676).
"Auricle." Stedman's Medical Dictionary 27th Edition. Online. Internet. Accessed Mar. 8, 2005 (cited in U.S. Appl. No. 10/391,676).
The American Heritage® Dictionary of the English Language, Fourth Edition, Copyright © 2009 by Houghton Mifflin Company (word: portion) (cited in U.S. Appl. No. 10/391,676).

* cited by examiner

*Primary Examiner* — Robert A Wax
*Assistant Examiner* — Danah Al-Awadi
(74) *Attorney, Agent, or Firm* — Martha A. Gammill

(57) ABSTRACT

A method of administering an antibiotic to an animal in need thereof, including the step of injecting the antibiotic subcutaneously at the junction of a pinna with the cranium of the animal, is disclosed.

10 Claims, 2 Drawing Sheets

METHOD OF ADMINISTERING AN INJECTABLE ANTIBIOTIC TO AN ANIMAL

CROSS REFERENCE TO RELATED APPLICATION

This application claims benefit of priority to U.S. patent application Ser. No. 10/391,676, filed Mar. 19, 2003 now abandoned, which claims benefit of priority to U.S. Provisional Application. Ser. No. 60/366,212 filed Mar. 21, 2002.

BACKGROUND OF THE INVENTION

1. Field of the Invention

The invention relates generally to a method of administering a drug to an animal, such as cattle, swine, sheep and goats, and, more particularly, the invention relates to a method of subcutaneously injecting an antibiotic to an animal.

2. Brief Description of Related Technology

The injection of many antibiotics produces irritation and, potentially, illegal drug residues at the injection site of food-producing animals. Current cattle practice is oriented toward changing from an intramuscular injection of drugs and vaccines, which leaves both irritation and possibly drug residues in edible meat, to subcutaneous injection, which places those unwanted occurrences at the surface of the carcass in cattle. Because the hide of cattle is removed at slaughter, the injection sites are potentially visible and will be trimmed from the carcass. Even if that is not done, the edible meat is not damaged because the injection is not made into muscle. Nevertheless, even with subcutaneous administration, injection site irritation and potentially violative drug residues still remain on an edible portion of the carcass, namely the surface of the carcass itself.

Furthermore, any violative drug residues at the injection site cannot be monitored by current United States Department of Agriculture (USDA) inspectors, who require a "target tissue" for residue monitoring to homogeneously contain drug residues and always be readily identifiable to the layman. These target tissues are now defined as the kidney, liver, muscle and fat; and an injection site in any edible tissue, regardless of whether the injection is intramuscular or subcutaneous, fails the criteria for a target tissue because the injection site is not always readily identifiable, circumscript or homogenous with respect to drug residues.

The only alternative for antibiotics which have injection site residues, that are unacceptable as target tissues, is to use surrogate target tissue with which to monitor residue depletion. In that case, the surrogate target tissue is not the tissue in which potentially unsafe residues reside, but rather is the circumscript and/or homogeneous tissue (with respect to incurred drug residues) for which residues can be monitored until the time after drug administration at which all other drug residues in tissues decrease to safe levels. Because it is a surrogate target tissue, residues must decrease to a much lower concentration than those determined to be safe for that tissue from toxicological studies and food consumption values, in essence, penalizing that tissue's safe concentration because it is being used as a surrogate for the injection site.

Ceftiofur crystalline free acid sterile oil suspension (CCFA-SS) is a sustained-release ceftiofur product that provides for prolonged absorption from an injection site and thus affords a single injection treatment of bacterial diseases in animals. The prolonged absorption of the drug from the injection site makes the injection site contain the highest concentration of drug residues for the longest period of time (several weeks) during which time the concentration in all other tissues decreases to non-detectable levels. This makes the use of a surrogate target tissue impossible for this antibiotic. This is not unique to ceftiofur crystalline free acid, but rather is common to all sustained-release injectable compounds. Thus, one common alternative has been to utilize the surrogate tissue approach described above, as a result of injection site residues remaining with the edible carcass of food-producing animals. A more recent alternative has been to inject the antibiotic subcutaneously in the posterior of the ear of the animal, according to the teachings of commonly-assigned Brown U.S. Pat. No. 6,074,657 (Jun. 13, 2001).

International Patent Publication No. WO 94/20505 (Sep. 15, 1994), discloses CCFA, its preparation and a method of administration. The examples in that publication describe that cattle were administered CCFA by injection intramuscularly (IM) or subcutaneously (SC) either in or on the edible tissues of the animals. At page 10 of the publication it refers to antibiotics implants disclosed in U.S. Pat. No. 5,079,007 (Jan. 7, 1992) and to various pharmaceutical dosage forms exemplified in U.S. Pat. No. 4,902,683 (Feb. 20, 1990).

The administration by injection of an antimicrobial formulation (e.g., ceftiofur crystalline free acid sterile suspension) subcutaneously in the neck, flank, posterior of the ear, or other subcutaneous sites on the edible-tissue portions of the carcass for the treatment of bacterial diseases, such as bovine respiratory disease (BRD) and swine respiratory disease (SRD) is known. The subcutaneous aural (i.e., ear) administration of hormones as solid dose implants is known. Implants of antibiotics are known but are typically administered intramuscularly in the edible tissues of the food-producing animal. Small-volume vaccines have been administered successfully intradermally in the ear of dogs and swine. Also in swine, diagnostic allergens and a vaccine in small volumes have been administered subcutaneously in the dorsal part or the posterior side of the ear. Injection of ceftiofur crystalline free acid sterile suspension subcutaneously in the posterior of the ear has been disclosed.

SUMMARY OF THE INVENTION

It is an objective of the invention to overcome one or more of the problems described above.

Accordingly, one aspect of the invention is a method of administering an antibiotic to an animal in need thereof, including the step of injecting the antibiotic subcutaneously at the junction of a pinna with the cranium of an animal.

Further aspects and advantages of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to the specific embodiments described herein.

DETAILED DESCRIPTION OF THE INVENTION

The invention is directed to a method of administering an antibiotic to an animal in need thereof, including injecting the antibiotic subcutaneously at the junction of a pinna with the cranium of the animal.

In a method according to the invention, the junction of a pinna with the cranium of an animal is selected for administration of an antibiotic by subcutaneous injection. In a preferred embodiment specifically, an antimicrobial sterile suspension injected subcutaneously in the junction of a pinna with the cranium. In the methods disclosed herein, a sufficient amount (from a residue standpoint) of the injection site is removed with the ear at the slaughterhouse.

Furthermore, administration specifically at the junction of a pinna with the cranium of an animal, according to a method disclosed herein, provides the added benefit of ease of administration, particularly the ability to administer the antibiotic to the animal without the use of a restraining mechanism such as a head gate or squeeze chute (e.g., when roped and bull-dogged in the pasture).

"Animals" as used herein include, but are not limited to, cattle, swine, sheep, and goats.

Figure 1:
FIG. 1 illustrates a method of administering an antibiotic according to one embodiment of the invention, showing a needle being inserted at the dorsocaudal portion of the junction of a left pinna with the cranium of an animal.
Figure 2:
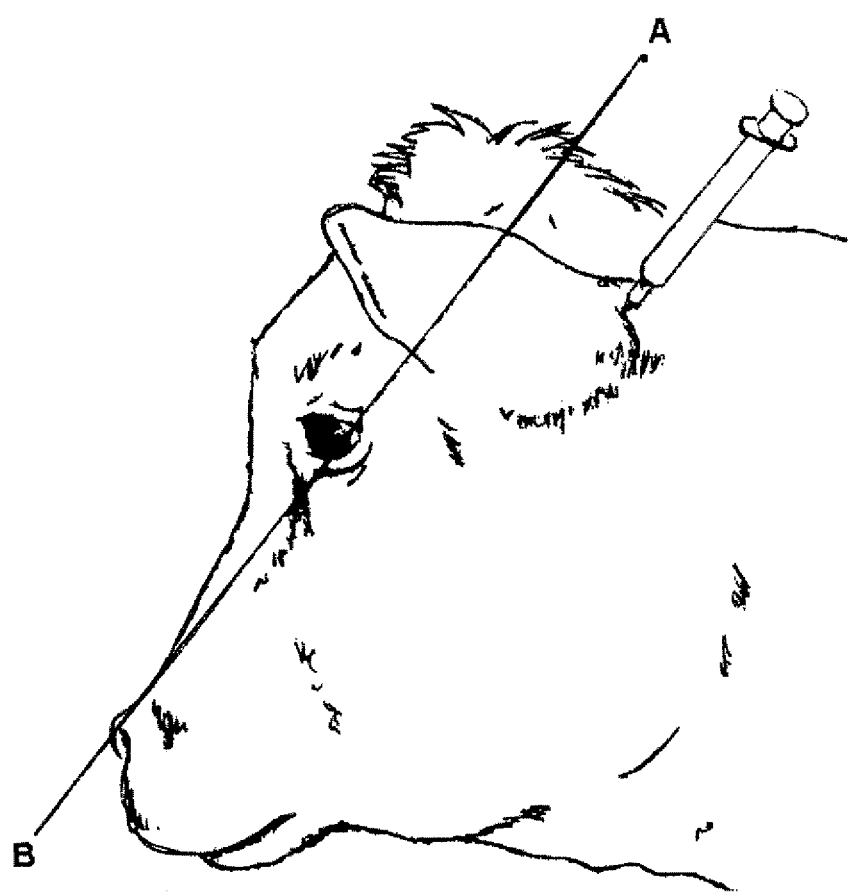
FIG. 2 is another illustration of a method of administering an antibiotic according to the invention, showing a needle being inserted at the dorsocaudal portion of the junction of a left pinna with the cranium of an animal with a reference line for the angle of injection according to a preferred embodiment.

According to a method disclosed herein, an antibiotic is injected at any point along the junction of a pinna (e.g., the auricular cartilage) with the cranium, preferably within the dorsocaudal half of the junction. FIGS. 1 and 2 provide visual representations of preferred methods of administration according to the invention wherein the junction is at the dorsocaudal portion of the junction of a pinna with the cranium. Preferably, a needle used for injection will be directed rostrally (i.e., toward the nose, see FIG. 2, guideline "A-B") from the caudal quarter of the junction of a pinna with the cranium. When the animal is selected from cattle, preferably the injection is caudal to the cervicoauricularis (superficialis, medius, and profundus) muscles, and dorsocaudal to the parotid salivary gland, which lies ventral to the auditory canal.

In one preferred method according to the invention when the animal is selected from cattle, injection is administered subcutaneously at the junction of a pinna with the cranium using a sterile needle (e.g., 16 gauge (G), 1.5 to 2.0 cm) (¾ inch) attached to a device such as a syringe, a repeating injector, a multi-dose syringe, and the like. The needle is directed caudal to the conchal eminence of the auricular cartilage, at the proximal end of the auricular cartilage near the base of the antiscaphal surface, and is directed rostrally from the caudal side of the ear. Preferably, injection is caudal to the cervicoauricularis muscles, and dorsocaudal to the parotid salivary gland. These anatomical specifications are applicable to other species in addition to cattle, although slight variations from species to species may occur. Once the needle is fully inserted, the drug administrator may draw back on a syringe plunger to assure that the needle is not in a blood vessel. Once in the subcutaneous tissue, an appropriate volume of injectable antibiotic is expelled through the needle, and the needle is subsequently withdrawn. Preferably, direct pressure is applied to the needle insertion point to minimize backflow of the injected material.

Even though the needle need not be inserted parallel to the skin (e.g., in preferred embodiments is injected perpendicular to the skin), the method is still considered a subcutaneous injection because of the short needle length and the location of the injection site.

Prior to administration, the animal's head may be stabilized (i.e. restrained) using a restraining mechanism such as a chin rest/head stabilizer on a squeeze chute, a head gate, or a halter. Advantageously, injection of an antibiotic as disclosed herein allows for administration without the use of such apparatus. Thus, for example, a stocker calf can be roped and bulldogged in the pasture, the ear of the target injection site can be gripped with the hand not holding the needle to stabilize the head of the animal, and the hand holding the needle can be used to perform the injection of the needle and delivery (e.g., discharge) of the antibiotic at the junction of a pinna with the cranium.

Needle injection is the preferred method of delivery, although use of syringes, automatic syringes, repeat-dose syringes, and injection guns can also be used in a similar manner.

One antibiotic suitable for use in a method disclosed herein is ceftiofur crystalline free acid (CCFA), which has the following formula I:

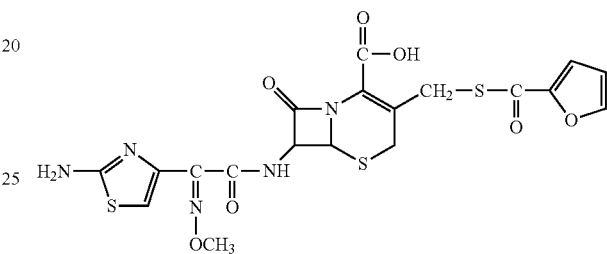

and is the crystalline form of the compound commonly known as ceftiofur, more properly named 7-[2-(2-amino-1,3-thiazol-4-yl)-2-methoxyimino)acetamido]-3-[(fur-2-ylcarbonyl)thiomethyl]-3-cephem-4-carboxylic acid (also named as 7-[2-(2-amino-4-thiazolyl)-2-(methoxyimino)acetamido]-3-[(2-furanylcarbonyl)thiomethyl)-8-oxo-5-thia-1-azabicyclo[4.2.0]oct-2-ene-1-carboxylic acid. CCFA, as well as formulations containing it and methods of their preparation, are described (particularly at pages 8-14) in International Patent Publication No. WO 94/20505 (Sep. 15, 1994), the entire disclosure of which is incorporated herein by reference.

Ceftiofur crystalline free acid sterile oil suspension (CCFA-SS) (100 mg/ml and 200 mg/ml) is a sustained-release ceftiofur formulation that provides for prolonged absorption from the injection site and thus affords a single injection treatment of bacterial diseases in animals. CCFA-SS is a prescription product for use in cattle for the treatment of the bacterial component of bovine respiratory disease associated with microorganisms susceptible to ceftiofur, such as *Mannheimia* spp. (i.e., *Pasteurella haemolytica*), *Pasteurella multicida* and *Haemophilus somnus*. In addition, CCFA-SS is a prescription product for use in swine for the treatment of the bacterial component of swine respiratory disease associated with microorganisms susceptible to ceftiofur, such as *Actinobacillus pleuropneumoniae, Streptococcus suis* and *S. parasuis*, and *P. multocida*.

Other antibacterial agents can be administered according to a method disclosed herein. These injectable antibiotics include the following: injectable suspensions of sparingly water-soluble antimicrobial agents, such as procaine penicillin, benzathine penicillin, ceftiofur crystalline free acid (CCFA), ceftiofur hydrochloride, ampicillin trihydrate and amoxicillin trihydrate; sustained-release non-aqueous solutions of sparingly water-soluble antimicrobial agents, such as oxytetracycline, erythromycin, tylosin, tilmicosin and florfenicol; and injectable solutions of zwitterionic antimicrobial agents, such as enrofloxacin, danofloxacin and premafloxacin. Amounts of these antibiotics effective to treat bacterial infections would be readily apparent to one of ordinary skill in the art. Examples of the approved forms, usages and dosages of these antibiotics, which are hereby incorporated by reference herein, appear in Veterinary Pharmaceuticals and Biologicals, 10th edition (1997) Veterinary Medicine Publishing Group, Lenexa, Kans., (page numbers indicated in parentheses): procaine penicillin (pages 422, 492 and 674-75), benzathine penicillin (pages 422, 492 and 675), ceftiofur hydrochloride (pages 550-51), ampicillin trihydrate (page 684), amoxicillin trihydrate (pages 427-28), oxytetracycline (pages 617-18 and 622), erythromycin (pages 547-48), tylosin (page 773), tilmicosin (page 630), florfenicol (page 652) and enrofloxacin (pages 448-49). U.S. Pat. No. 5,563,155 (Oct. 8, 1996), which is hereby incorporated by reference herein, describes quinolone-type antibacterial agents, including premafloxacin. The effective dosage range of CCFA is 1.1 mg CE (ceftiofur equivalents)/kg BW (body weight) to 8.8 mg CE/kg BW when administered SC at the base of the ear as a single injection. More preferably, the dosage range is 4.4 mg CE/kg BW to 6.6 mg CE/kg BW daily. A method according to the invention can be used to deliver the typically large quantities or volumes of these antibiotic formulations, such as from one ml to fifteen ml.

Injection of CCFA subcutaneously at the junction of a pinna with the cranium of cattle provides for sustained release of the drug from an injection site that is largely removed with the ear and, therefore, will be of reduced human food safety concern. Currently, the ears of cattle are not considered edible by the United States Government according to USDA regulations, and the ears, including the base of the ear, are removed from cattle at slaughter. Thus, other tissues may be used as the target tissue, using the concentrations in those tissues that is deemed to be safe from toxicological studies and food consumption factors. Using this scenario, CCFA may have a short slaughter withdrawal time, because residues in all edible tissues will be below the safe concentrations determined for each tissue by FDA/CVM within a few days after administration. This is a great advantage from a customer standpoint because the method can be easily used in the pasture and it is not necessary to wait an extended period to slaughter the animals. Furthermore, the method provides significant consumer safety attributes because the locus of substantial drug residues from sustained-release injectable products, namely the injection site, resides in tissue that is not consumed by human beings.

Administration of CCFA to cattle using the junction of a pinna and the cranium as the location for injection is expected to provide therapeutic equivalence to administration in the middle third of the posterior of the ear.

CCFA may also be administered SC at the junction of a pinna and the cranium either at arrival processing or for the treatment of BRD (usually early in the feedlot stay) in combination with growth-promoting steroid implants administered in approximately the same location and time at arrival processing. Advantageously, administration according to a method disclosed herein can be performed in the pasture.

Similar advantages and results are expected from the use of the method of the invention to administer CCFA and other antibiotics to animals in need thereof, as fully described above.

EXAMPLES

Example 1

Residue Decline in Edible Tissues

A CCFA sterile suspension was administered at the junction of a pinna and the cranium of 42 Angus crossbred beef cattle aged 6-12 months (242 kg to 342 kg) using a sterile 16G ¾-inch (2.5 cm) needle a concentration of 200 mg ceftiofur equivalents/mL of formulation at a dose of 6.6 mg CE/kg BW as a single injection. Two additional cattle served as non-treated controls. The cattle were randomly assigned to seven slaughter groups of six (3 males and 3 females) for slaughter at 12, 24, 48, 72, 96, 120, and 240 hours following the administration of CCFA-SS. Blood samples were obtained prior to drug administration and at 12, 24, 48, 72, 96, 120, 144, 168, and 240 hours after drug administration from the 240-hour slaughter group. At necropsy, inedible ear tissues were removed using routine slaughterhouse practices, and edible tissues adjacent to the removed inedible tissues ("injection site" tissues) were then harvested. Inedible tissues include ear cartilage and salivary gland tissue and were not included in the "injection site" tissue samples.

The average residue concentrations in the edible "injection site" tissue were 178.8 µg CE/g 12 hours after administration, peaked at 405.9 µg CE/g 48 hours after administration, then decreased to 28.4 µg CE/g 240 hours after administration. While higher than the injection site resides remaining on the edible carcass when injectable antibiotic formulations are administered in the middle third of the ear, the residues are substantially less than after subcutaneous administration in the neck. This is because a substantial fraction of the residues at the injection site are removed with the inedible tissues of the ear. The average duration the concentration of ceftiofur and desfuroylceftiofur-related residues remained above 0.2 µg/mL in the plasma was 238 hours. Kidney residues decline in a similar fashion to that observed after subcutaneous administration in the middle third of the posterior side of the ear. In both cases, mean residue values never exceed 3 µg CE/g, and decrease to less than 0.5 µg CE/g between 5 and 10 days after injection.

The results of PK analyses were conducted using WIN-NONLIN software. The PK parameters $AUC_{0-LOQ}$ and $t_{>0.2, \, model}$ had estimated mean values of 414 (±66.4) µg·h/mL and 238 (±17.9) hours, respectively. By comparison, using subcutaneous administration in the middle third of the posterior ear, the $AUC_{0-LOQ}$ averaged 376 µgh/mL, whereas the $t_{>0.2, \, model}$ averaged 183 hours. These results are consistent with expected therapeutic equivalence of the two methods of administration (middle third of the posterior ear versus at the junction of a pinna with the cranium).

The foregoing description is given for clearness of understanding only, and no unnecessary limitations should be understood therefrom, as modifications within the scope of the invention may be apparent to those having ordinary skill in the art.

What is claimed is:

1. A method for treating a bacterial infection in an animal in need thereof comprising injection of an effective amount of an antibiotic subcutaneously at the junction of a pinna with the cranium of the animal, wherein the animal is cattle and the injection is caudal to the cervicoauricularis muscles and dorsocaudal to the parotid salivary gland.

2. The method of claim 1, wherein the injection is within the dorsocaudal half of the junction.

3. The method of claim 1 wherein the antibiotic is selected from the group consisting of procaine penicillin, benzathine penicillin, ceftiofur crystalline free acid, ceftiofur hydrochloride, ampicillin trihydrate, amoxicillin trihydrate, oxytetracycline, erythromycin, tylosin, tilmicosin, florfenicol, enrofloxacin, danofloxacin, and premafloxacin.

4. The method of claim 1 wherein the antibiotic is crystalline ceftiofur free acid of formula I

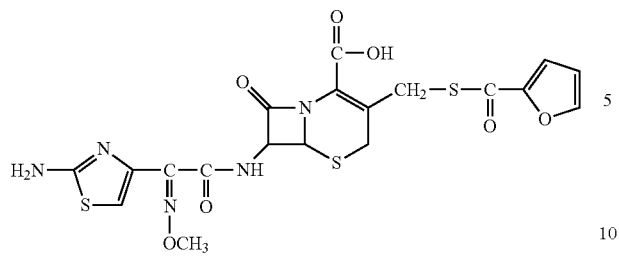

which is 7-[2-(2-amino-1,3-thiazol-4-yl)-2-methoxy-imino)acetamido]-3-[(fur-2-ylcarbonyl)thiomethyl]-3-cephem-4-carboxylic acid.

5. The method of claim 4, wherein crystalline ceftiofur free acid is in a sterile oil suspension.

6. The method of claim 5, wherein the injected volume of the formulation is from about 1 ml to about 15 ml.

7. The method of claim 6, wherein the antibiotic is injected with a single syringe needle.

8. The method of claim 1, wherein the bacterial infection is bovine respiratory disease.

9. The method of claim 4, wherein the amount of ceftiofur crystalline free acid is from about 1.1 to about 8.8 mg/kg of body weight.

10. The method of claim 9, wherein the amount of ceftiofur crystalline free acid is from about 4.4 to about 6.6 mg/kg of body weight.

* * * * *